(12) United States Patent
Kaplan et al.

(10) Patent No.: US 7,888,459 B2
(45) Date of Patent: Feb. 15, 2011

(54) IN VACUO GLYCATION OF PROTEINS

(75) Inventors: Harvey Kaplan, Ottawa (CA); Mary Catherine King, Ottawa (CA); Nicolas Andre Stirling Stewart, Frederick, MD (US)

(73) Assignee: Anhydrovac Inc., Thornhill, Ontario (CA)

( * ) Notice: Subject to any disclaimer, the term of this patent is extended or adjusted under 35 U.S.C. 154(b) by 248 days.

(21) Appl. No.: 10/524,547

(22) PCT Filed: Aug. 15, 2003

(86) PCT No.: PCT/CA03/01233

§ 371 (c)(1),
(2), (4) Date: Oct. 26, 2005

(87) PCT Pub. No.: WO2004/016645

PCT Pub. Date: Feb. 26, 2004

(65) Prior Publication Data

US 2006/0122369 A1 Jun. 8, 2006

(30) Foreign Application Priority Data

Aug. 15, 2002 (CA) .................................. 2398213

(51) Int. Cl.
*A61K 38/14* (2006.01)
*A61K 38/00* (2006.01)
*A61K 51/00* (2006.01)
*C07K 9/00* (2006.01)

(52) U.S. Cl. .................... 530/322; 514/1.1; 424/1.69

(58) Field of Classification Search ................ 530/322
See application file for complete search history.

(56) References Cited

U.S. PATENT DOCUMENTS 4,971,954 A * 11/1990 Brodsky et al. ............... 514/21
5,955,438 A 9/1999 Noff et al.

OTHER PUBLICATIONS

Boratynski Janusz: "Dry reaction of proteins with carbohydrates at 120 degrees C yield neoglycoconjugates" Biotechnology Techniques, vol.12, No. 9, Sep. 1998, p. 707-710, XP009022491 (In IDS 5/05 & PCT/CA03/01233).*
Boratynski Janusz et al: "High temperature conjugation of proteins with carbohydrates" Glycoconjugate Journal, vol. 15, No. 2, Feb. 1998, p. 131-138, XP009022617 (In IDS 5/05 & PCT/CA03/01233) (abstract provided).*
Tarelli Edward et al: "Lysine vasopressin undergoes rapid glycation in the presence of reducing sugars" Journal of Pharmaceutical & Biomedical Analysis, vol.12, No. 11, 1994, p. 1355-1361, XP009022490 (abstract provided).*
Boratynski, J.: "Dry reaction of proteins with carbohydrates at 120 degrees C yield neoglycoconjugates" Biotechnology Techniques, vol.12, No. 9, Sep. 1998, p. 707-710, XP009022491 (In IDS 5/05 & PCT/CA03/01233).*
Boratynski, J. et al: "High temperature conjugation of proteins with carbohydrates" Glycoconjugate Journal, vol. 15, No. 2, Feb. 1998, p. 131-138, XP009022617 (In IDS 5/05 & PCT/CA03/01233) (abstract provided).*
Tarelli et al: "Lysine vasopressin undergoes rapid glycation in the presence of reducing sugars" Journal of Pharmaceutical & Biomedical Analysis, vol.12, No. 11, 1994, p. 1355-1361, XP009022490 (abstract provided).*
Ledl et al. Angew Chem. Int. Ed. Engl. (Jun. 1990), 29(6), 565-594.*
Taralp Alpay et al: "Chemical modification of lyophilized proteins in nonaqueous environments" Journal of Protein Chemistry, vol. 16, No. 3, 1997, p. 183-193, XP009022573.

* cited by examiner

*Primary Examiner*—Maury Audet
(74) *Attorney, Agent, or Firm*—Heenan Blaikie LLP; Adrian M. Kaplan

(57) ABSTRACT

It has been discovered that facile glycation of proteins can be achieved by colyophilization of a protein with a reducing sugar, subjecting the lyophilized mixture to a vacuum (10 to 50 millitor) and incubating at an elevated temperature (50 to 100° C.) for 1 to 24 h. A stable ketoamine derivative is formed with amino groups in the protein and no advanced glycation end products (browning reaction) are observed, as is the case with aqueous glycation procedures. Another novel feature is that the in vacuo glycation reaction takes place with the protonated amine and not the deprotonated amine as is believed to be the case for aqueous glycation reactions. Advantage can be taken of the in vacuo glycation reaction to achieve facile covalent cross-linking of proteins by lyophilizing protein or proteins with compounds containing two or more reducing sugars separated by a linker.

5 Claims, 6 Drawing Sheets

A

B

IN VACUO GLYCATION OF PROTEINS

FIELD OF THE INVENTION

The invention relates to a method of glycating proteins or material containing at least one amino group.

BACKGROUND OF INVENTION

Glycoproteins are involved in a wide variety of multivalent interactions that are of physiological importance. The many potential roles of carbohydrates covalently attached to proteins are of interest in theoretical structure-function studies and practical applications. In particular, applications such as increasing the stability and solubility of proteins (Sundaram, P. V. and Venkatesh, R., 1998, *Protein Eng.*, 11, 699-705, Ed.), (Aoki, T., Hiidome, Y., Kitahata, K., Sugimoto, Y., Ibrahim, H. R. and Kato, Y., 1999, *Food Res. Int.*, 32, 129-133, Ed.) and the development of vaccines (Mammen, M., Choi, S.-K. and Whitesides, G., 1998, *Angew. Chem. Int. Ed.*, 37, 2754-2794, Ed.), (Wong, S. Y., 1995, *Current Opin. Struct. Biol.*, 5, 559-604, Ed.), (Roy, R., 1996, *Current Opin. Struct. Biol.*, 6, 692-702, Ed.) have spurred efforts to discover efficient methods of chemical attachment of carbohydrate to proteins, i.e. glycation. Protein glycation is often carried out under aqueous conditions where the reaction is unfavorable due to the fact that water is a product. Current aqueous glycation methods also require relatively large amounts of protein and carbohydrate (Yeboah, F. K., Alli, I. and Yaylayan, V. A., 1999, *J. Agric. Food Chem.*, 47, 3164-3172, Ed.), (Roy, R., Katzenelenbogen, E. and Jennings, H. J., 1984, *Can. J. Biochem. Cell Biol.*, 62, 270-275, Ed.), and the extent of glycation is very difficult to control (Wrodnigg, T. M. and Eder, B., 2001, *Glycoscience*, 215, 115-152, Stutz, A. E., Ed., Springer-Verlag). Another significant drawback is that the desired glycation product, cyclic ketoamine, is contaminated with advanced glycation products (Wrodnigg, T. M. and Eder, B., 2001, *Glycoscience*, 215, 115-152, Stutz, A. E., Ed., Springer-Verlag), (Yaylayan, V. A. and Huyghues-Despointes, A., 1994, *Crit. Rev. Food Sci. Nutrition*, 34, 321-369, Ed.) i.e Maillard browning reaction.

An effective method of increasing the efficiency of a reaction is by the removal of a product. The first step in the glycation of an amino group is believed to be the reaction of a deprotonated amine with the aldehyde group of a reducing sugar yielding water and a Schiff base as products (Yaylayan, V. A. and Huyghues-Despointes, A., 1994, *Crit. Rev. Food Sci. Nutrition*, 34, 321-369, Ed.), (Wrodnigg, T. M. and Eder, B., 2001, *Glycoscience*, 215, 115-152, Stutz, A. E., Ed., Springer-Verlag). In aqueous media, formation of the Schiff base is reversible, and in situ reductive alkylation of the Schiff base forming a stable derivative has been employed to achieve efficient glycation (Cayot, P., Roullier, L. and Tainturier, G., 1999, *J. of Agric. & Food Chem.*, 47, 1915-1923, Ed.), (Wrodnigg, T. M. and Eder, B., 2001, *Glycoscience*, 215, 115-152, Stutz, A. E., Ed., Springer-Verlag). Theoretically, another way of promoting the glycation reaction is by the removal of the water but there is no obvious experimental approach for such a strategy under aqueous conditions. Water could be removed by carrying out the reaction in the dry state under vacuum. Dry state glycation has been attempted under a variety of conditions (Boratynski, J. and Roy, R., 1998, *Glycoconjugate J.*, 15, 131-138, Ed.), (Boratynski, J., 1998, *Biotechnol. Tech.*, 12, 707-710, Ed.), (Quan, C. P., Wu, S., Dasovich, N., Hsu, C., Patapoff, T. and Canova-Davis, E., 1999, *Anal. Chem.*, 71, 4445-4454, Ed.), (Morgan, F., Leonil, J., Molle, D. and Bouhallab, S., 1999, *J. Agric. Food Chem.*, 47, 83-91, Ed.), (Yeboah, F. K., Alli, I., 1999, *J. Agric. Food Chem.*, 47, 3164-3172, Ed.), (French, S. J., Harper, W. J., Kleinholz, N. M., Jones, R. B. and Green-Church, K. B., 2002, *J. Agric. Food Chem.*, 50, 820-823, Ed.) but a common observation is that many glycation products are observed and the mechanism of their formation is unclear. None of these studies have used a vacuum to promote the glycation reaction by the removal of water or to prevent the formation of advanced glycation end products.

Amino groups in dry proteins are present in their protonated form, and for glycation to take place, the reaction would have to involve these protonated amino groups. On the basis of current theory, a protonated amino group in solution does not react with the aldehyde form of a reducing sugar. Furthermore, there is no known theory that predicts that if a mixture of a protein and reducing sugar in the dry state were subjected to a vacuum that a water-stable glycated derivative would be formed. The fact that extensive glycation of proteins does occur in the lyophilized state under vacuum with heating demonstrates that the protonated amino group does indeed react. Therefore, there are two novel theoretical features to the discovery that lyophilized proteins can be efficiently glycated in vacuo in the dry state: 1. A protonated amino group will react with a sugar aldehyde group in vacuo. 2. A ketoamine derivative is formed which does not rapidly revert to the free amine and sugar when placed in aqueous solution.

Covalent cross-linking of proteins is a major tool for the study of structure-function relationships in proteins and has many practical applications (Fancy, D. A., 2001, *Curr. Opin. Chem. Biol.*, 4, 28-33, Ed.), (Phizicky, E. M., 1995, *Microbiol. Rev.*, 59, 94-123, Ed.), (Lundblad, R., 1994, *Techniques in Protein Modification*, 249-261, Ed., CRC Press). Homobifunctional reagents with variable spacing between the reactive groups have been widely used to achieve such cross-links (Lundblad, R., 1994, *Techniques in Protein Modification*, 249-261, Ed., CRC Press). To our knowledge, reducing sugars have never been used as bifunctional reagents for the cross-linking of proteins. However, the discovery of the facile glycation that occurs in vacuo indicates that a reagent with two or more reducing sugars with variable spacing could be used to covalently cross-link proteins in the lyophilized state. The ideal number of spacer units separating the reducing sugars depends on the protein or proteins being cross-linked. In general, the ideal number of units will likely be less than 10 but in some applications could be much greater. The cross-linking methodology would be identical to the in vacuo glycation with reducing sugars.

In vacuo glycation is easier to carry out than aqueous glycation. It requires only co-lyophilization of appropriate amounts of protein and reducing sugar followed by incubation at an elevated temperature under vacuum. In addition, in vacuo glycation has several other significant technical advantages.

1. The procedure can be carried out using a wide range of protein and/or carbohydrate quantities, viz. gram to picogram quantities.
2. The protein can be lyophilized at a pH value where it retains its native structure and biological activity.
3. The extent of glycation is easily controlled either by adjusting the protein/carbohydrate ratio or by the addition of excipients.
4. Elevated temperatures can be used to increase the rate of glycation without structural damage to the protein or carbohydrate.
5. With proteins, no contaminating advanced glycation products (Maillard browning reaction) are observed. Only the ketoamine derivative is observed.

6. Complex carbohydrates or compounds containing two or more reducing sugars can be used to cross-link proteins.

There is therefore a need for a facile method of glycating proteins.

SUMMARY OF INVENTION

The invention provides a method of glycating proteins and of achieving covalent cross-linking of proteins.

The invention is the glycation (non-enzymatic covalent attachment of sugars) of proteins by the use of an in vacuo reaction of a reducing sugar with one or more amino groups to form a stable ketoamine derivative(s). Reducing monosaccharides or more complex carbohydrates or compounds containing at least one reducing sugar can be employed. The extent of glycation can be controlled by incubation temperature, protein/reducing sugar ratio, addition of excipients (e.g. trehalose) and pH of lyophilization. The in vacuo glycation reaction can be used to achieve covalent cross-linking of proteins by the use of carbohydrates or compounds containing two or more reducing sugars.

According to one aspect of the invention there is provided a method of glycating a protein comprising the following steps:

combining a quantity of one of a reducing sugar and a reducing polysaccharide with the protein in a solution
lyophilizing the solution to produce a lyophilized sample;
placing said lyophilized sample under vacuum; and
heating said lyophilized sample under vacuum.

According to another aspect of the invention, there is provided a method of glycating a protein comprising the following steps:

combining a linker including at least two reducing sugars with the protein in a solution;
lyophilizing the solution to produce a lyophilized sample;
placing said lyophilized sample under vacuum; and
heating said lyophilized sample under vacuum.

According to another aspect of the invention there is provided a method of glycating a protein comprising the following steps:

combining a linker including at least two reducing sugars with the at least two proteins in a solution;
lyophilizing the solution to produce a lyophilized sample;
placing said lyophilized sample under vacuum; and
heating said lyophilized sample under vacuum.

According to yet another aspect of the invention there is provided a method of glycating a protein comprising the following steps:

combining a linker including at least two reducing sugars with a protein
lyophilizing the solution to produce a lyophilized sample;
placing said lyophilized sample under vacuum;
heating said lyophilized sample under vacuum.
isolating the glycated monomeric product
combining the glycated monomeric product with a protein
lyophilizing the solution to produce a lyophilized sample;
placing said lyophilized sample under vacuum; and
heating said lyophilized sample under vacuum at a temperature in the range of about 40° to about 150° C.

DETAILED DESCRIPTION OF INVENTION

Materials and Methods

Materials

Figure 1:
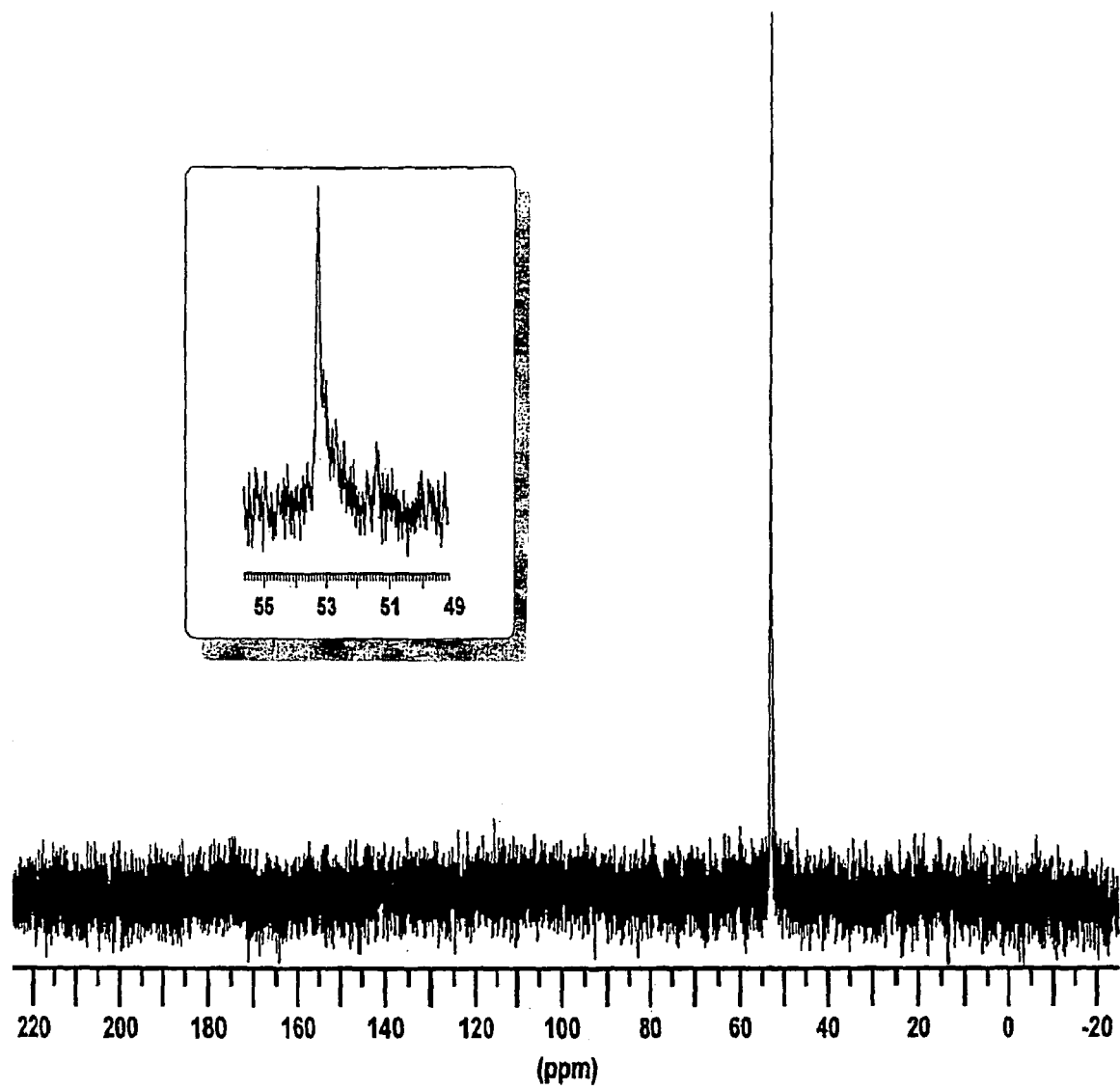
FIG. 1 is a Solution $^{13}$C NMR of glycated RNase with $^{13}C_1$-D-glucose. Inset: Expanded region of the predominant peak.

Ribonuclease A (Sigma R-4875) from bovine pancreas and human hemoglobin (Sigma H-7379) were purchased from Sigma Chemical Company and used without further purification.

D-[U-$^{14}$C] glucose (310 mCi/mmol), 50 μCi in 250 μl aqueous solution containing 3% ethanol was purchased from Amersham Pharmacia Biotech. D-Glucose-1-$^{13}$C, 99 atom % $^{13}$C, was purchased from Sigma Chemical Company. All other chemicals, reagents and solvents used were high purity preparations obtained from commercial sources.

In Vacuo Glycation of Lyophilized Proteins

Typically, protein was added to a glucose solution for a final ratio of 5:1 or 10:1 protein/glucose (w/w). The pH of the solution was adjusted with 1M HCl or NaOH, via microsyringe, to the desired pH (6.5 to 10). Aliquots of protein/reducing sugar solutions were transferred to borosilicate test tubes and frozen by immersing in liquid nitrogen. The samples were subsequently lyophilized to room temperature. The tubes, containing the lyophilized protein/reducing sugar mixture, were narrowed and sealed under vacuum ($1$-$50 \times 10^{-3}$ torr) with an oxygen-enriched flame, placed in an oven at 65° C. and left to react for a controlled period of time (2 to 24 hours).

In Vacuo Glycation with D-[U-$^{14}$C] Glucose

Trace radio-glycation of RNase was prepared by dissolving RNase (20 mg, 1400 nmol) in dH$_2$O (10 ml), adding D-[U-$^{14}$C] glucose solution (20 μl, 13 nmol; see above), adjusting the pH with 1M NaOH (pH 6.5 or 10) and lyophilizing as described above.

A hemoglobin/glucose solution (10:1 w/w) was prepared containing D-[U-$^{14}$C] glucose 37.5 nCi per mg of protein. After application of the in vacuo reaction procedure, samples were dissolved in 10% glucose solution to displace un-reacted D-[U-$^{14}$C]glucose and extensively dialyzed against dH$_2$O.

Aliquots of the protein/reducing sugar solution (50 μl) were transferred to scintillation vials before and after dialysis, scintillation cocktail (5 ml) (Aquasol-2, DuPont) was added and the samples were counted for 10 minutes on a Beckman LS 6500 multi-purpose scintillation counter using the $^{14}C$ window. Protein amount was normalized by recording absorbance at 280 nm on a Pharmacia Biotech Ultraspec 2000 UV/V is spectrophotometer with $dH_2O$ as blank.

In Vacuo Glycation with D-[1-$^{13}$C] Glucose

RNase (106.54 mg) was dissolved in 50 ml $dH_2O$ in a 250 ml RB flask, D-glucose-1-$^{13}$C (10.60 mg) was added to the protein solution, the pH was raised to 10 with 1 M NaOH and the solution was frozen/shelled in $N_2(l)$ and lyophilized.

The lyophilized protein: reducing sugar mixture was transferred to a borosilicate hydrolysis tube and glycated as above for 24 hours.

NMR Spectroscopic Analysis

RNAse glycated with D-Glucose-1-$^{13}$C was extensively dialysed against $dH_2O$ (MWCO 3500), lyophilized and dissolved in $^2H_2O$ (99.9 atom % $^2H$, Cambridge Isotope Laboratories) and the $^{13}$C-NMR spectrum was acquired on a Bruker spectrometer operating at 9.4 Tesla ($^{13}$C, 100.6 MHz) for 600 scans using the DEPT 135 pulse sequence (Sanders and Hunter, 1987).

Synthesis of Sugar Cross-linkers

Bifunctional cross-linkers containing reducing sugars separated by a spacer (FIG. 4a) were synthesized from glucose derivatives. Glucosamine or glucuronic acid are glucose derivatives which contain functional groups through which the spacer can be coupled, a carboxylic group in the former and an amino group in the latter. Bis acids and amines of vary lengths were used to furnish the linear spacers and were coupled to the appropriate glucose derivative using a water-soluble carbodiimide (1-ethyl-3-(3-dimethylaminopropyl) carbodiimide). Branched cross-linkers were synthesized from glucuronic acid and polypropyleneimine dendrimer (Generation 1.0) (FIG. 4b) using O-(7-azabenzotriazol-1-yl)-N,N,N',N'-tetramethyluroniumhexafluorophosphate (HATU) as coupling agent.

In Vacuo Cross-linking Reaction Method

Typically, a stock solution of accurately weighed protein/mL of distilled $H_2O$ was prepared and, depending on the experiment, the pH was adjusted with either 1N NaOH or 1N HCl. Aliquots of the protein stock solution of a minimum volume of 500 μL to yield between 2-5 mg protein/tube, were transferred to 13×100 mm borosilicate glass disposable culture tubes to which varying aliquots of a solution of cross-linker dissolved in distilled $H_2O$ were added. The tubes were left to stand for approximately 10-15 minutes and were then flash frozen and lyophilized. The tubes were then sealed under vacuum using an oxygen-enriched flame and incubated at 60° C.-85° C. for a period of 12-18 hours. The protein was reconstituted with 0.5 mL of distilled $H_2O$ and analyzed by SDS-PAGE, HPLC or FPLC.

SDS-PAGE Analysis of Cross-linked Proteins

Sodium dodecyl sulphate polyacrylamide gel electrophoresis was performed using a Bio-Rad Mini-PROTEAN II dual slab cell apparatus. All reagents and molecular weight markers were purchased from BioRad or Sigma, and were electrophoresis grade quality (buffers were prepared as required using $dH_2O$). Approximately 10 μg of protein/well was loaded onto a 12% polyacrylamide gel and electrophoresis was conducted at a constant current of 20-25 mA/gel (with a voltage gradient of 70-150 mV) under discontinuous gel conditions. Coomassie Brilliant Blue G250 was used to stain the protein bands in the gel following electrophoresis.

Results and Discussion

Solution $^{13}$C NMR of glycated RNase with $^{13}C_1$-D-glucose reveals that only one product is present. The single resonance peak, located at 53.2 ppm in FIG. 1, corresponds to the cyclic ketoamine adduct (Neglia, C. I., Cohen, H. J., Garber, A. R., Ellis, P. D., Thorpe, S. R. and Baynes, J. W., 1983, *J. Biol. Chem.*, 258, 14279-14283, Ed.). It is particularly notable that no advanced glycation end-products (browning reaction) are present as is the case in conventional non-reductive glycation procedures (Yaylayan, V. A. and Huyghues-Despointes, A., 1994, *Crit. Rev. Food Sci. Nutrition,* 34, 321-369, Ed.). Conventional glycation procedures require the use of a reducing agent such as sodium borohydride to form a stable amino alcohol derivative and prevent the production of advanced glycation end-products. Another advantage of the in vacuo glycation procedure is that no additional reaction is required to stabilize the glycation product as it yields a stable ketoamine product directly.

Figure 2:
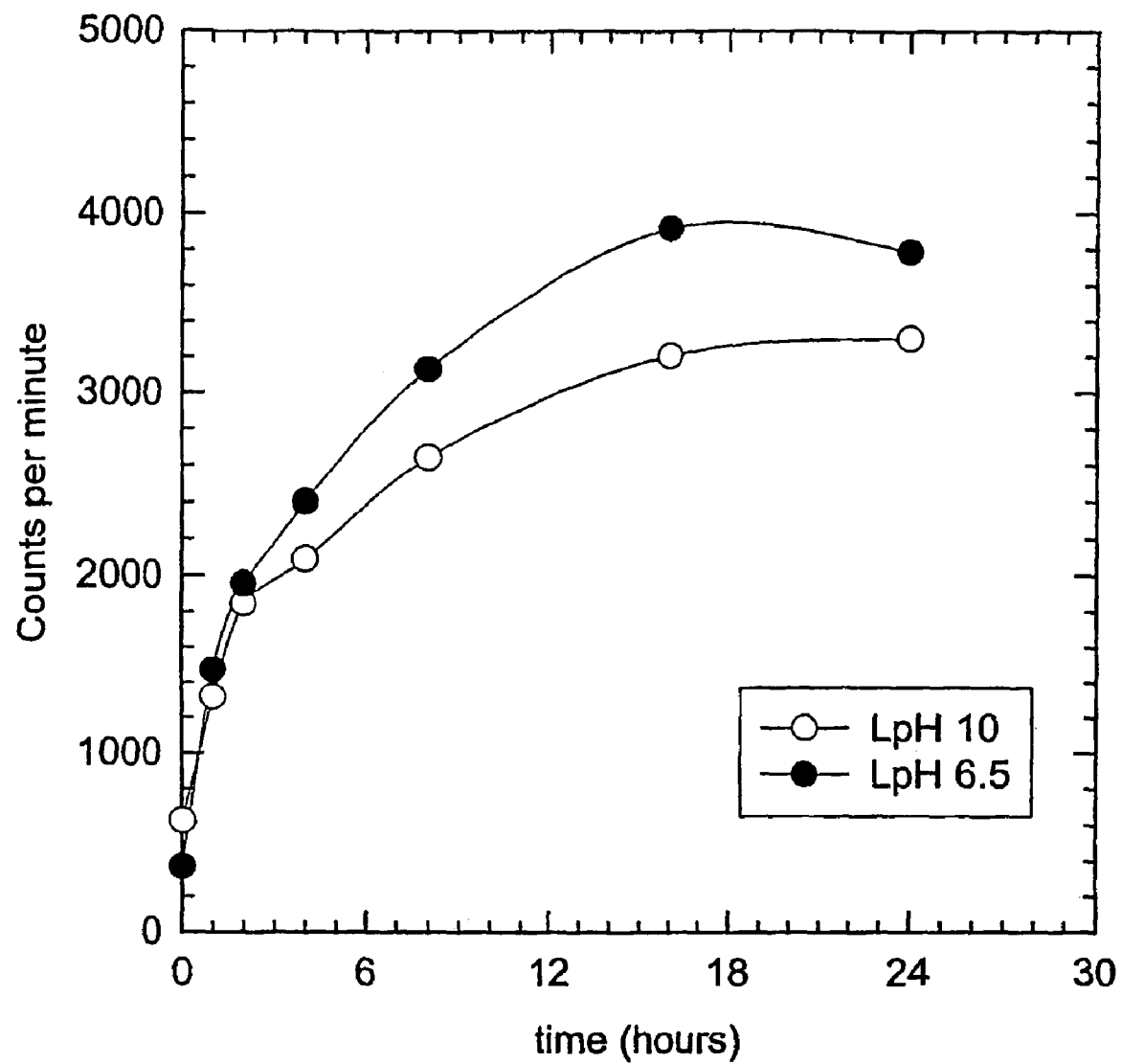
FIG. 2 is a plot showing time course and effect of pH of lyophilization on in vacuo glycation. RNase with a trace of $^{14}$C-[U]-glucose was lyophilized at pH 6.5 and pH 10, heated incubated at 65° C. for up to 24 hours.
Figure 3:
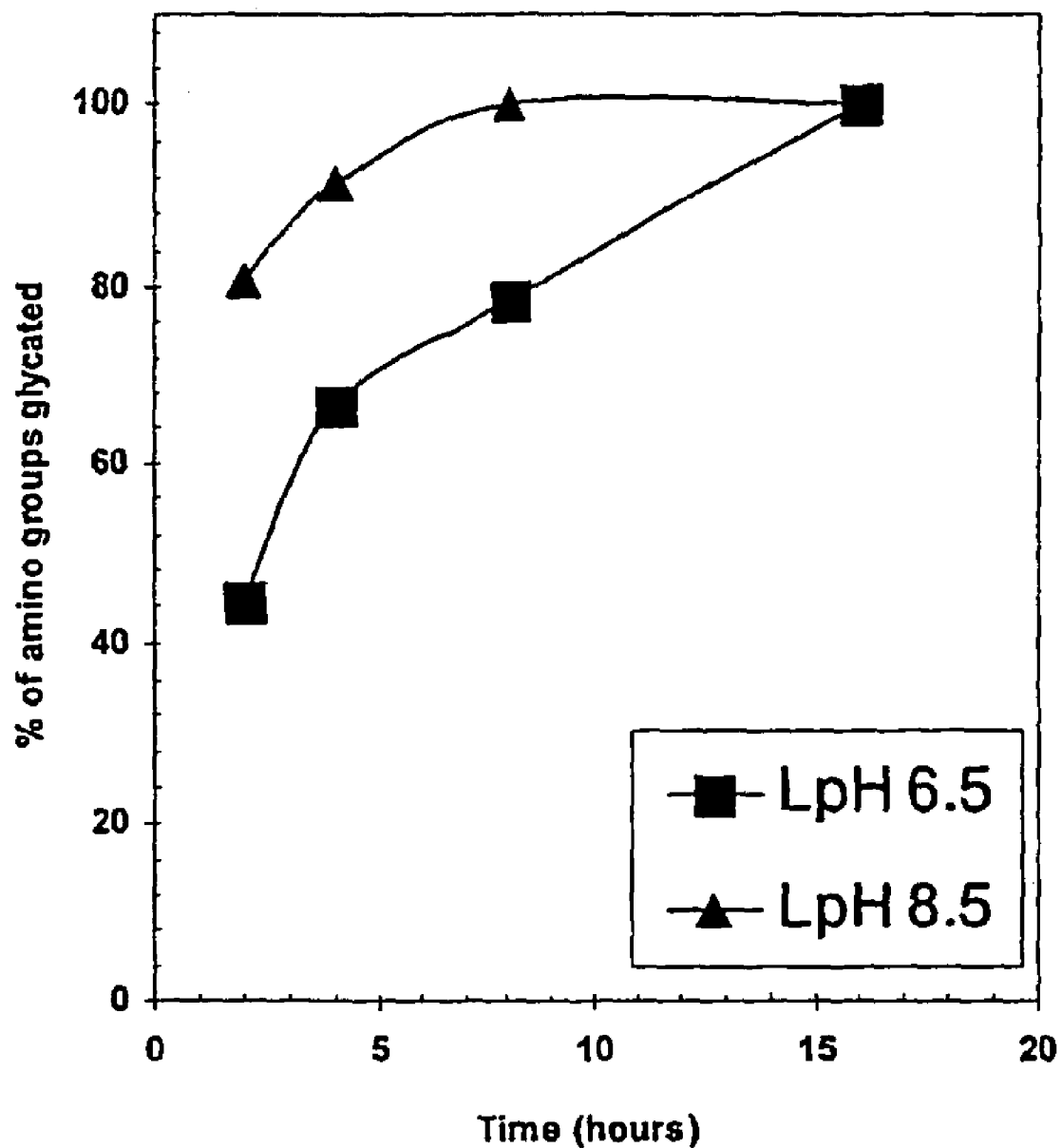
FIG. 3 is a plot showing extent of in vacuo glycation of lyophilized human hemoglobin incubated 65° C., based on 48 possible glycation sites.

D-[U-$^{14}$C] glucose (310 mCi/mmol) was used directly as supplied without addition of any unlabeled glucose to determine the rate of glycation using the in vacuo procedure. FIG. 2 shows that the rate of incorporation at pH 6.5 and pH 10 is very similar and is essentially complete after 12 hours with incubation at 65° C. FIG. 3 shows that within experimental error all the amino groups of hemoglobin can effectively be glycated by the in vacuo glycation procedure.

The accepted mechanism for the glycation in water involves the nuleophilic attack of a proteins amino group on the open chain form of the reducing sugar forming a Schiff base which undergoes Amadori rearrangement to form the ketoamine derivative. As lysine ε-amino groups in proteins normally have ionization constants of 10.5 to 11, very little glycation of amino groups would be expected below pH 10.5 where the protonated form of the amino group predominates. However, the results in FIG. 3 show that the protonated form of the amino group is readily glycated by the in vacuo procedure. The mechanism by which this glycation occurs has not been established but it is clearly different from that postulated for glycation in solution.

Figure 4:
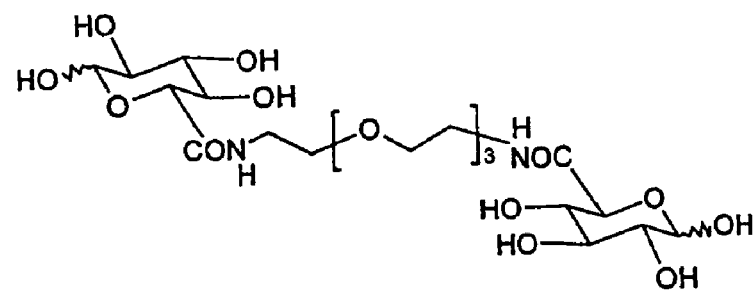
FIG. 4 is a plot showing A—4,7,10-trioxa-1,13-tridecanediglucuronamide (TTDG) B—polypropyleneiminetetraglucuronamide dendrimer (PTGD).
Figure 4:
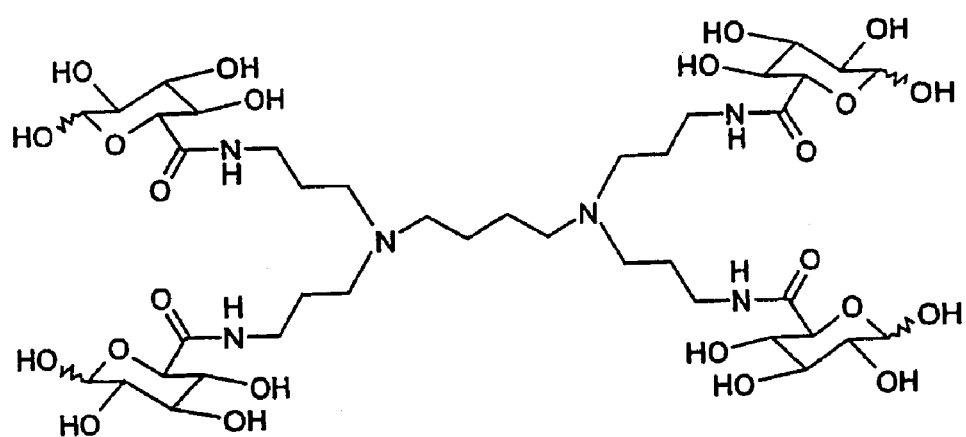
Figure 5:
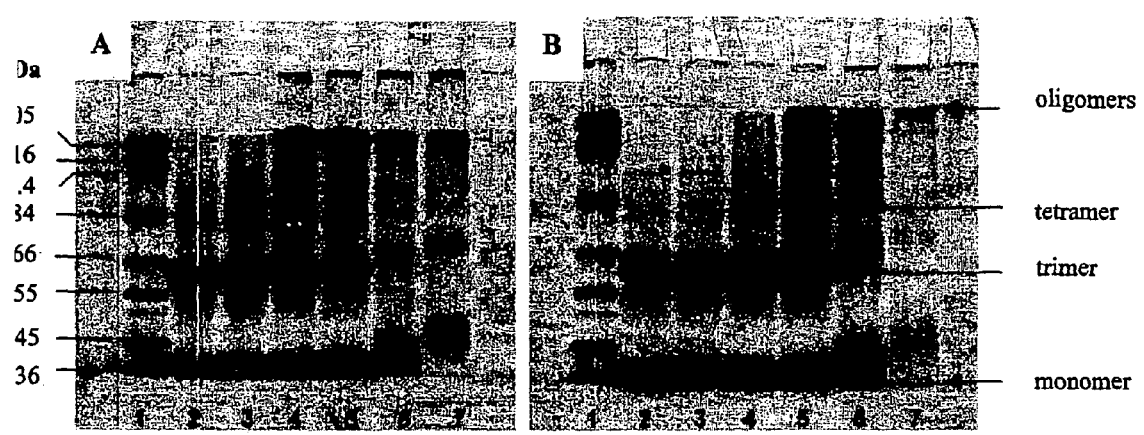
FIG. 5 is a SDS-PAGE of human hemoglobin (Hb) co-lyophilized with increasing concentrations of the homobifunctional cross-linker TTDG at pH 10.0 (adjusted with 1 N NaOH) A) with trehalose (0.6 mg/mg Hb), B) without trehalose, and heated at 60° C. for 20 hours under vacuum. Concentrations in each lane expressed as moles TTDG/mole Hb: Lane 1-MW markers; Lane 2—0; Lane 3—0.2; Lane 4—1; Lane 5—2; Lane 6—10; Lane 7—20.
Figure 6:
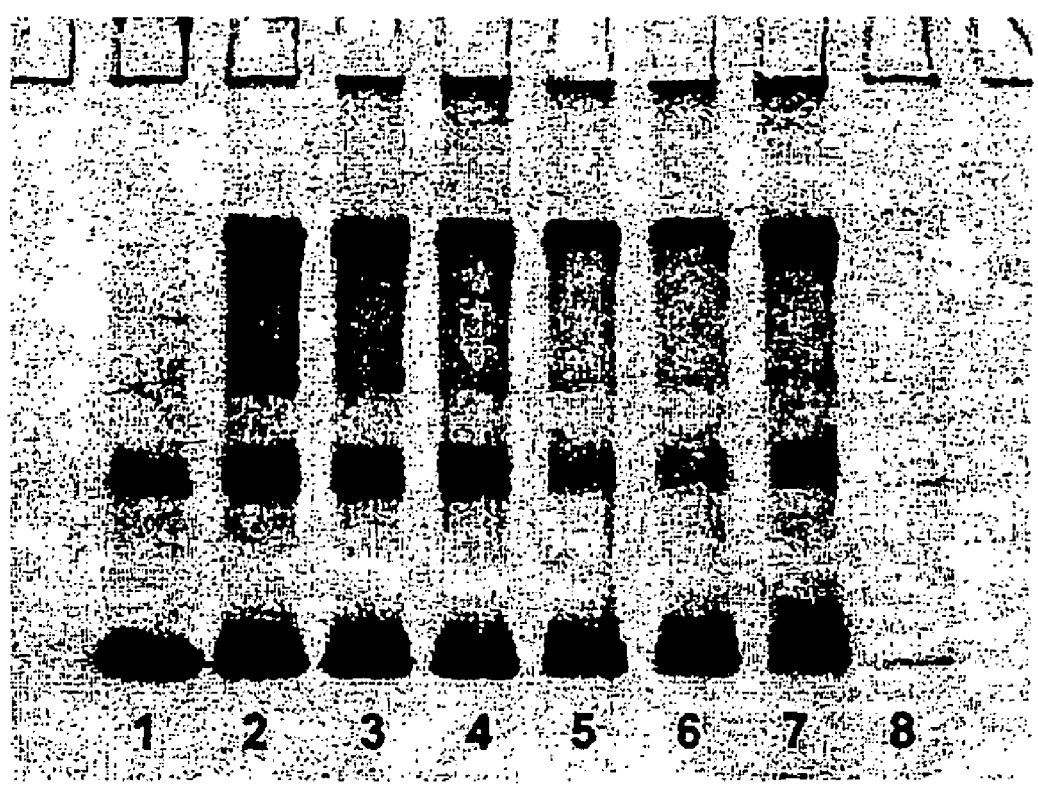
FIG. 6 is a SDS-PAGE showing cross-linking between human hemoglobin (Hb) and increasing amounts of the branched cross-linker PTGD co-lyophilized at pH 5.8 (unadjusted) and heated under vacuum at 65° C. for 19 hours. Concentrations in each lane expressed as moles PTGD/mole Hb: Lane 1:0; Lane 2—0.2; Lane 3—0.5; Lane 4—0.7; Lane 5—1; Lane 6—1.2; Lane 7—1.5; Lane 8-MW markers.

The in vacuo glycation methodology has been used to develop a new class of protein cross-linking reagents, viz. linear bifunctional and multifunctional branched glyco-crosslinkers. Two such cross-linking reagents have been synthesized, 4,7,10-trioxa-1,13-tridecanediglucuronamide (TTDG) (FIG. 4a) and polypropyleneiminetetraglucuronamide dendrimer (PTGD) (FIG. 4b). FIG. 5 shows cross-linking of human hemoglobin with increasing amounts of the bifunctional glyco-crosslinker TTDG using the in vacuo glycation methodology. Substantial amounts of dimer and higher oligomers of cross-linked hemoglobin are clearly visible (FIG. 5a) with SDS-PAGE, as well some insoluble, very highly cross-linked material that does not enter the gel. FIG. 5b shows the effect of the addition of an excipient, trehalose which promotes the formation of soluble cross-linked oligomers. The glycation procedure with the branched glyco-crosslinker PTGD also yields substantial amounts of dimer and higher oligomers of hemoglobin (FIG. 6).

CONCLUSIONS

The results obtained in the present study show that facile glycation of proteins can be achieved by an in vacuo reaction of the protein with a reducing sugar or compounds containing one or more reducing sugars. The in vacuo glycation procedure can be used with linear bifunctional and multifunctional branched glyco-derivatives containing reducing sugars to achieve facile covalent cross-linking of proteins.

From the foregoing, it will be appreciated that, although specific embodiments of the invention have been described herein for purposes of illustration, various modifications may be made without deviating from the spirit and scope of the invention.

REFERENCES

1. Sundaram, P. V. and R. Venkatesh, Retardation of thermal and urea induced inactivation of a-chymotrypsin by modification with carbohydrate polymers. Protein Eng., 1998. 11(8): p. 699-705.
2. Aoki, T., et al., Improvement of heat stability and emulsifying activity of ovalbumin by conjugation with glucuronic acid through the Maillard reaction. Food Res. Int., 1999. 32: p. 129-133.
3. Mammen, M., S.-K. Choi, and G. Whitesides, Polyvalent Interactions in Biological Systems: Implications for Design and Use of Multivalent Ligands and Inhibitors. Angew. Chem. Int. Ed., 1998. 37: p. 2754-2794.
4. Wong, S. Y., Current Opin. Struct. Biol., 1995. 5: p. 559-604.
5. Roy, R., Current Opin. Struct. Biol., 1996. 6: p. 692-702.
6. Yeboah, F. K., I. Alli, and V. A. Yaylayan, Reactivities of D-glucose and D-fructose during glycation of bovine serum albumin. J. Agric. Food Chem., 1999. 47: p. 3164-3172.
7. Roy, R., E. Katzenellenbogen, and H. J. Jennings, Improved procedures for the conjugation of oligosaccharides to protein by reductive amination. Can. J. Biochem. Cell Biol., 1984. 62: p. 270-275.
8. Wrodnigg, T. M. and B. Eder, The Amadori and Heyns rearrangements: landmarks in the history of carbohydrate chemistry or unrecognized synthetic opportunities?, in Glycoscience, A. E. Stutz, Editor. 2001, Springer-Verlag: New York. p. 115-152.
9. Yaylayan, V. A. and A. Huyghues-Despointes, Chemistry of Amadori rearrangement products: analysis, synthesis, kinetics, reactions, and spectroscopic properties. Crit. Rev. Food Sci. Nutrition, 1994. 34(4): p. 321-369.
10. Cayot, P., L. Roullier, and G. Tainturier, Electrochemical modifications of proteins. 1. Glycitolation. J. of Agric. & Food Chem., 1999. 47(5): p. 1915-1923.
11. Boratynski, J. and R. Roy, High temperature conjugation of proteins with carbohydrates. Glycoconjugate J., 1998. 15: p. 131-138.
12. Boratynski, J., Biotechnol. Tech., 1998. 12: p. 707-710.
13. Quan, C. P., et al., Susceptibility of rhDNase I to glycation in the dry-powder state. Anal. Chem., 1999. 71: p. 4445-4454.
14. Morgan, F., et al., Modification of bovine b-lactoglobulin by glycation in a powdered state or in an aqueous solution: effect on association behavior and protein conformation. J. Agric. Food Chem., 1999. 47: p. 83-91.
15. French, S. J., et al., Maillard reaction induced lactose attachment to bovine b-lactoglobulin: electrospray ionization and matrix-assisted laser desorption/ionization examination. J. Agric. Food Chem., 2002. 50: p. 820-823.
16. Fancy, D. A., Curr. Opin.Chem. Biol., 2001. 4: p. 28-33.
17. Phizicky, E. M., Microbiol. Rev., 1995. 59: p. 94-123.
18. Lundblad, R., in Techniques in Protein Modification. 1994, CRC Press: Boca Raton, FL. p. 249-261.
19. Neglia, C. I., et al., 13C NMR investigation of nonenzymatic glucosylation of protein. J. Biol. Chem., 1983. 258 (23): p. 14279-14283.

The invention claimed is:

1. A method of glycating a protein comprising the following steps:
   combining a quantity of a reducing sugar with the protein in a solution;
   lyophilizing the solution to produce a lyophilized sample;
   placing said lyophilized sample under vacuum; and
   heating said lyophilized sample under vacuum,
   whereby a water-stable ketoamine derivative with amino groups in the protein, which does not rapidly revert to the free amine and sugar when placed in aqueous solution, is formed.

2. A method according to claim 1 wherein the sample is heated at a temperature in the range of about 40° C. to about 150° C.

3. A method according to claim 1 wherein the reducing sugar is heated from 1 to 48 hours.

4. A method according to claim 1 wherein the reducing sugar is selected from the group consisting of 1 to 50 sugar units.

5. A method according to claim 1 wherein the protein is lyophilized from a solution in the range of pH 2 to pH 12.

* * * * *